United States Patent [19]
Kriz

[11] Patent Number: 4,499,770
[45] Date of Patent: Feb. 19, 1985

[54] SYSTEMS FOR MONITORING CHANGES IN ELASTIC STIFFNESS IN COMPOSITE MATERIALS

[75] Inventor: Ronald D. Kriz, Boulder, Colo.

[73] Assignee: The United States of America as represented by the Secretary of Commerce, Washington, D.C.

[21] Appl. No.: 400,571

[22] Filed: Jul. 22, 1982

[51] Int. Cl.³ .......................................... G01N 29/00
[52] U.S. Cl. ........................................ 73/599; 73/570; 73/577
[58] Field of Search ......................... 73/599, 570, 577

[56] References Cited

PUBLICATIONS

"Ultrasonic Attenuation as an Indicator of Fatigue Life of Graphite Fiber Epoxy Composites", Williams, Jr. et al., *Materials Evaluation*, May 1980, pp. 33-37.

*Primary Examiner*—Howard A. Birmiel
*Attorney, Agent, or Firm*—Eugene J. Pawlikowski; Alvin J. Englert; Donald W. Margolis

[57] ABSTRACT

Traversing energy flux transmitted into a fiber/matrix composite structure is propagated through the structure in directions which vary depending upon the elastic stiffness condition of the composite. Degradation in elastic stiffness of the composite, from any cause, will result in variations in the direction of travel of the flux through the composite. By determining the direction of flux propagation in the composite, or the portion of the composite structure from which the flux is detected as it exits the structure, the condition of the composite structure, independent of the source of degradation, can be determined. In preferred embodiments the energy flux is ultra-sound energy, while in preferred testing devices a single transmitting transducer is directed towards at least two receiving transducers, for example, one located at a position to receive some flux in the total absence of stiffness degradation, and a second located at a position to receive some flux which would have traveled through a stiffness degraded structure.

13 Claims, 3 Drawing Figures

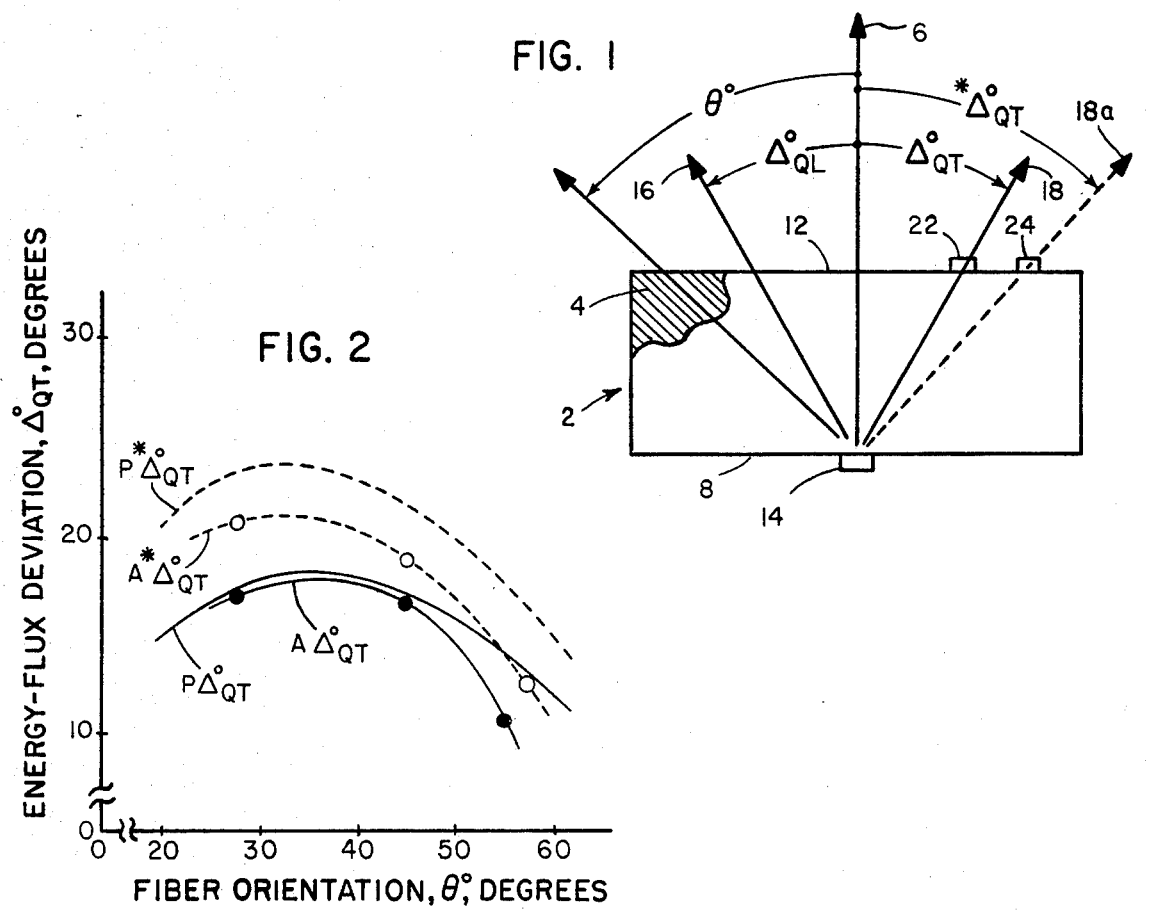
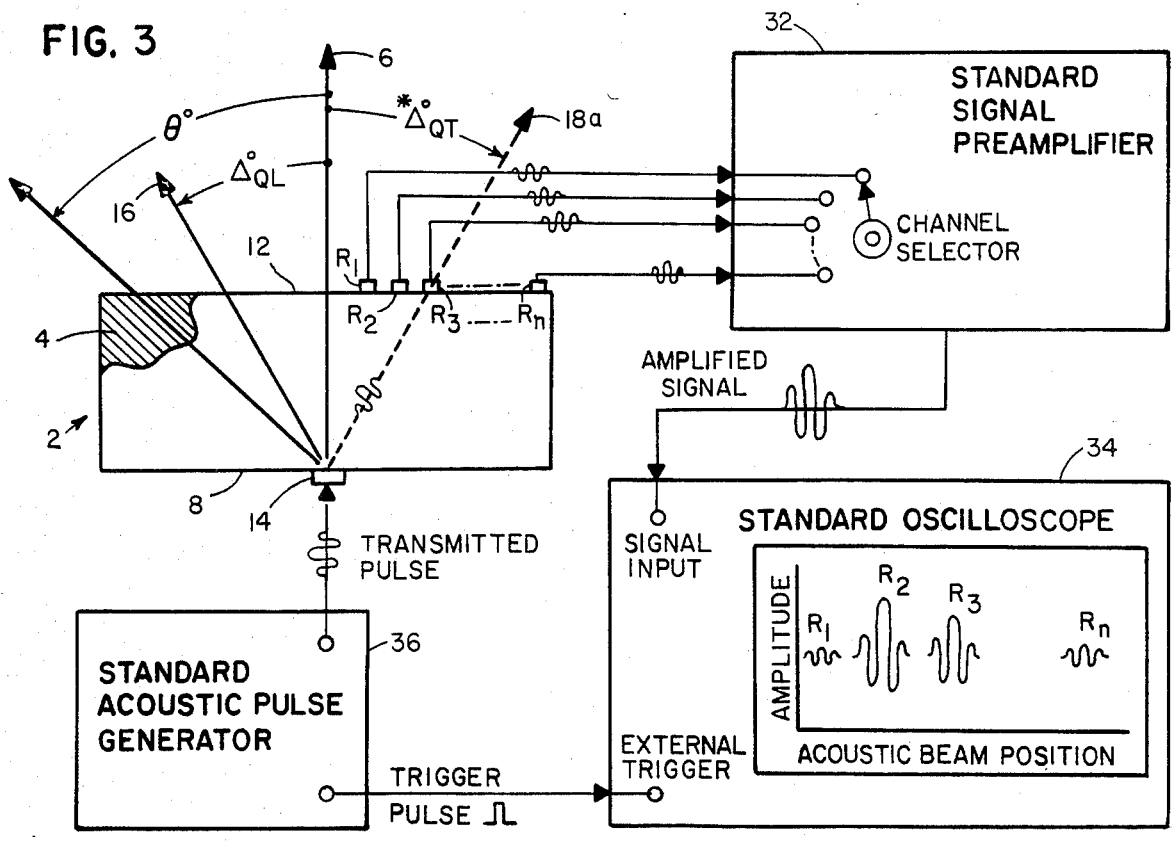

SYSTEMS FOR MONITORING CHANGES IN ELASTIC STIFFNESS IN COMPOSITE MATERIALS

BACKGROUND OF THE INVENTION

1. Field of the Invention

The present invention relates to methods and apparatus for measuring and testing the condition of composite materials. More particularly it relates to ultra-sound systems for determining and measuring stiffness degradation of fiber/matrix composite structures whether caused by moisture, heat or cold, radiation, chemicals, or any other source of degradation.

2. Description of the Prior Art

As composite materials become more widely used, especially in stiffness critical structural designs, such as tolerance sensitive high technology and aerospace systems, the ability to monitor the stability and integrity of the materials becomes more and more important.

U.S. Pat. No. 4,221,962 (Black, et al) discloses a method for detecting the presence of moisture, and thus degradation due to moisture, in the interior of fiber/matrix composite structures by embedding a radiation carrier, such as an optical fiber, inside of the structure, and then transmitting radiation through the radiation carrier. Changes in moisture in the structure effect the index of refraction of the radiation carrier, and thus provide a measurable indication of the moisture in and therefore the degradation of the structure due to moisture. However, the presence of moisture in a composite cannot always be associated with a degradation in a composite. Additionally the system of Black, et al requires the production of special composite materials, with an intrusive testing portion, and cannot be applied to composites in general.

R. D. Kriz and W. W. Stinchcomb, Elastic Moduli of Transversely Isotropic Fibers and Their Composites, J. Exp, Mech. 19, 41–49 (1979) demonstrated that it is possible to predict and measure the direction of energy flux propagation within a graphite/epoxy composite whose fibers are unidirectionally aligned at 45 degrees from the wave normal direction. However, this publication does not anticipate nor suggest measurement of changes in any such properties as an indication of the condition or of the degradation of such composites.

Other art includes: R. D. Kriz, Absorbed Moisture and Stress Wave Propagation in Graphite/Epoxy, Poster session presented at Defense Advanced Research Projects Agency/Air Force Materials Laboratory Review of Progress in Quantitative NDE, Aug. 2, 1981, Boulder, Colo.; and R. D. Kriz, Absorbed Moisture and Stress Wave Propagation in Graphite/Epoxy, Comp. Tech. Rev., Spring 1982; and R. D. Kriz, Monitoring Elastic Stiffness Degradation in Graphite/Epoxy Composites, Conference Proceedings for American Society for Nondestructive Testing, Boston, Mass., March, 1982; (Abstract concurrently in print, disclosing basic concepts and relationships now set forth in more detail and claimed in the present application).

Other than the latter three references, authored by the inventor of the present invention; none of the above cited prior art, nor any other known prior art, utilized, recognizes nor suggests monitoring changes in the direction of propagation or the deviation of energy flux transmitted into and through such composites.

SUMMARY OF THE INVENTION

It has been discovered that changes in the elastic stiffness properties of fiber/matrix composite structures are measured by propagating energy flux stress waves through the composite material, and then measuring changes in the angle of the flux as an indication of elastic stiffness degradation. In describing the present invention it must be understood that this technique is substantially only applicable to specific forms of fiber/matrix composites. It is applicable to composites in which the matrix or binder material is isotropic and in which the fibers within the matrix are undirectional. An "isotropic" matrix is one which exhibits physical properties, such as stiffness, having the same values when measured along any axis or in any direction. Fibers within such a matrix are considered to be "unidirectional" when they are substantially all oriented in substantially the same longitudinal direction and are also all substantially parallel to one another. Unless the contrary is indicated, it shall be understood that throughout this specification and claims, that when the term "matrix" is used it shall mean "isotropic matrix" and that all fibers in such a matrix are "unidirectional".

Such composite structures to which the systems of the present invention can be applied may include materials in fiber form, including, for example; graphite and other forms of carbon, glass, various polymers, boron, tungsten, and mixtures thereof and other art known fibers. However, as used in the present invention, the fibers are always arrayed unidirectionally within the matrix. Matrix or binder materials may include, for example, various thermoset polymers, such as epoxies and phenolics, various thermoplastic polymers, such as polyimide, or various metals such as copper or aluminum and other art known matrix materials. However, as used in the present invention such matrix materials when formed into a composite are isotropic. Fibers may constitute from about 1% to about 91%, by volume, of the composite, although fiber volumes of about 50% to about 70% are most common.

Fiber/matrix composites, when formed, have been found to have excellent properties, generally combining light weight with good stiffness and strength. However, such composites have a shortcoming, composites have been found to be subjected to degradation due to the effects or conditions of, for example, temperature change, moisture, radiation, chemical aging, and due to other changes in the composition of the materials utilized to form the composite structure. For example, normally, absorbed moisture will affect a fiber/matrix composite structure by increasing its weight, and decreasing its stiffness. Radiation may either increase or decrease the stiffness of the composite structure, depending upon the composition of the matrix material. Normally, increases in the temperature of the composite structure will decrease its stiffness while conversely a decrease in temperature will normally increase the structure's stiffness. Chemical aging of the structure will increase or decrease the stiffness of the structure, depending upon the specific nature of the aging. For example, loss of plasticizers or increased polymerization of a polymeric matrix material, from any cause, will normally increase the stiffness of the structure, while absorbtion of solvents, water, or work fatigue will normally reduce the stiffness of the structure. In any event, regardless of the cause of the change in stiffness, these and other phenomena can and do result, over time, in changes in the stiffness of fiber/matrix composite structures. In some forms of use it is important to have a means for measuring such changes of stiffness. In some special structures it is also important, to have the ability to constantly or periodically measure and verify, in situ, the stiffness or degradation of fiber/matrix composite structures. Clearly therefore the ability to have a means for non-destructively and non-invasively measuring stiffness degradation in every type and form of fiber/matrix composite material, in the laboratory or in situ, is useful.

It has now been found that such a system is simply, and effectively provided by transmitting a relatively discrete energy flux into a given portion of a composite structure, and then determining the direction of propagation of that flux within the structure or the portion of the structure from which the flux is detected as it exits the structure, and then, over time, any deviation in the direction of such flux propagation. Thus by determining the deviation in flux, or by determining the portion of the structure from which the flux exits, or the relative strength of the flux as it exits from different portions of the structure, the condition of the fiber/matrix composite material can be determined.

In preferred embodiments, of the present invention, the energy flux is ultra-sound and equivalents thereof. In preferred systems of the present invention this process may be carried out, for example, by locating at least one transmitting transducer in a position to direct energy flux, such as ultra-sound into the structure, and providing at least two receiving transducers at positions opposed to the transmitter to receive and measure the energy flux which is transmitted through the structure as it exits the structure.

In the simplest and most preferred embodiment, only a single transmitting transducer would be utilized, and only two receiving transducers need to be utilized. In such a system, one receiving transducer is located at a position to receive some amount of flux traveling through an undegraded fiber/matrix composite structure, while the second receiving transducer is located at a position to receive some amount of flux as it would be deviated after traveling through a degraded composite structure. Where only two, or a plurality of receiving transducers less than a continuous array are utilized, the condition of the structure is determined by comparing the strength of the energy flux received by each receiving transducer. The change in signal strength at each transducer can be used to determine the change or shift in directions of propagation of the energy flux, which change or shift is indicative of the degradation of the composite structure.

In an alternative embodiment, again utilizing a single transmitting transducer, a continuous array of receiving transducers may be located at the surface of the structure opposed to the transmitter. By utilizing such a continuous array of receiving transducers, the condition of the structure can be determined either as it varies continuously, or at any instant in time.

In the practice of the present invention, using ultrasound as the energy flux, it is found that as the energy enters the composite it is divided into a longitudinal or quasi-longitudinal component, designated $\Delta°_{QL}$, and a transverse or quasi-transverse component, designated $\Delta°_{QT}$. It has been found that only the shift in the quasi-transverse component is of use in determining the condition of the composite. In preferred embodiments the angle or direction of the unidirectional fibers in the composite are known or determined, and the angle of propagation of the energy flux through the composite is measured relative to the wave normal vector. In some instances, changes in the condition of the composite structure can be measured without knowing the angle of the fibers.

It is therefore, an object of this invention to provide a simple, inexpensive method and apparatus for monitoring and detecting the elastic stiffness condition of fiber/matrix composite structures, and of assemblies constructed utilizing such structures.

It is a further object of this invention to provide means for detecting the elastic stiffness condition of such a fiber/matrix composite structure without destroying or invading the structure, and without affecting its structural properties.

Other objects and advantages inherent in this invention will readily be seen with reference to the ensuing specification and drawings.

DESCRIPTION OF THE DRAWINGS

FIG. 1 provides a diagrammatic representation of the process and system of the present invention wherein a partially broken away fiber/matrix composite structure is shown in relation to an acoustic energy flux transmitter and a pair of acoustic energy flux receivers.

FIG. 2 is a graph showing data which predicts and then experimentally verifies the relationship between the energy-flux deviation for undegraded and for degraded fiber/matrix composite structures having different fiber orientations.

FIG. 3 shows a system, similar to FIG. 1, in which an array of acoustic energy flux receivers is utilized, and in which related portions of a testing system are represented.

DESCRIPTION OF THE PREFERRED EMBODIMENTS

As shown in FIG. 1 fiber/matrix composite structure 2 having fibers 4, as represented at the partially broken away portion, substantially all oriented unidirectionally and substantially parallel to one another at an angle $\theta$ as measured from vector 6 which is perpendicular to both lower surface 8 and upper surface 12 of composite 2. In the practice of the present invention composite structure 2 has acoustic energy-flux transmitter 14 positioned substantially adjacent and parallel to lower surface 8. Energy-flux transmitter 14 is used to transmit acoustic energy-flux into composite structure 2. Upon entering structure 2 the energy generated by transmitter 14 bifurcates into two acoustic beams which are represented by their center line vectors 16 and 18 and designated, due to their particle displacements, as "quasi-longitudinal" (QL) and "quasi-transverse" (QT), respectively.

Composite structure 2 carries at least two acoustic energy-flux receivers 22 and 24 positioned apart from one another and substantially adjacent to and parallel to upper surface 12. Receiver 22 is optimally located at a position either measured or predicted to receive the maximum or a substantial amplitude of the QT flux portion 18 of the bifurcated beam transmitted from transmitter 14 after it passes through fiber/matrix structure 2 in a substantially undegraded state at some angle $\Delta°_{QT}$ measured from vector 6. Receiver 24 is optimally located at a position either measured or predicted to receive the maximum or a substantial amplitude of the QT flux portion 18a of the bifurcated energy beam as it would be transmitted from transmitter 14 and passed through fiber/matrix structure 2 at an angle $*\Delta°_{QT}$ after structure 2 has been subjected to substantial degradation. The angle $*\Delta°_{QT}$ is also measured from vector 6.

Now referring again to FIG. 1, the operation of the system can be more fully described and explained with regard to the elastic anisotropy resulting from the unidirectional alignment of the fibers. In isotropic matrix structures without fibers the elastic properties have the same values when measured along any axis or in any direction. If structure 2 had no fibers 4, then propagation of energy-flux from transmitter 14, in the form of an acoustic beam, would traverse the isotropic matrix structure, without fibers, parallel to normal vector 6 and perpendicular to lower surface 8. However, in structures with fibers 4 unidirectionally aligned at some angle $\theta$ from normal vector 6 the structure becomes anisotropic and varies according to the angle of orientation of the fibers. It is believed that the anisotropy of the structure's elastic constants, when it includes fibers, provides preferred paths along which acoustic energy flux will traverse the fiber/matrix composite structure. When fibers 4 are unidirectionally aligned at some angle $\theta°$ from the normal vector 6 the preferred paths of acoustic energy flux traverse the structure 2 from transmitter 14 along bifurcated acoustic beam propagation directions 16 and 18. These preferred paths of bifurcated acoustic energy-flux are measured as deviations from the normal vector 6 where $\Delta°_{QT}$ and $\Delta°_{QL}$ measures propagation direction of the quasi-transverse and quasi-longitudinal acoustic beam centerlines respectively. This bifurcation and deviation of energy-flux propagation from the normal vector 6 can be predicted as a function of the fiber alignment $\theta°$ and elastic properties of the fiber and matrix materials. Any change in either the fiber alignment $\theta°$, or in the elastic properties of fibers 4 and/or the elastic properties of the matrix component will change the direction of the path along which quasi-transverse energy-flux component propagates. By measuring the change in the the relationship between the deviation angle $\Delta°_{QT}$ and the fiber orientation angle $\theta$ or the perpendicular 6, or the original angle, the state of the structure can be determined. Such angles, both measured and predicted, are illustrated in FIG. 2 for a graphite/epoxy fiber/matrix composite structure at a fiber volume fraction of 67 percent.

Stiffness variation, indicative of degradation of either the matrix or binder material of composite structure 2 will result in a change of $\Delta°_{QT}$ to some angle $*\Delta°_{QT}$. With receivers 22 and 24 fixed in their respective positions a change in the direction of the QT portion of the bifurcated energy flux beam from an initial or undegraded $\Delta°_{QT}$ vector or position to a degraded vector or position $*\Delta°_{QT}$ can be determined in situ by monitoring the relative amplitudes of the QT energy component at both receivers 22 and 24. Interestingly, the vector position of the QL portion of the bifurcated energy beam transmitted from transmitter 14 after it passes through the same fiber/matrix structure 2 at an angle $\Delta°_{QL}$ from vector 6 is apparently not affected or varied by degradation of the matrix or fiber material.

Now referring to FIG. 2, we find represented energy flux deviation angles for fiber/matrix composite structures having various angles of fiber orientation. Curve $P\Delta°_{QT}$ represents the predicted $\Delta°_{QT}$ for undegraded graphite/epoxy composites having their fibers oriented at various angles, while closely related curve $A\Delta°_{QT}$ represents the $\Delta°_{QT}$ actually measured. In a similar manner curve $P*\Delta°_{QT}$ represents the predicted $*\Delta°_{QT}$ for degraded graphite/epoxy composites, while closely related curve $A*\Delta°_{QT}$ represents the $*\Delta°_{QT}$ actually measured for the composite material. It is thus seen that for graphite/epoxy composite structures having a wide range of fiber orientations there is a definite and measurable (and quite predictable) change in the quasi-transverse acoustic beam when the fiber/matrix composite undergoes degradation. It is noted that no changes in the deviation angle $\Delta°_{QL}$ are predicted nor have they been measured for either a degraded matrix component alone or for a fiber/matrix composite structure.

Now, referring to FIG. 3, in which like reference numbers refer to like portions as in FIG. 1, a testing system is shown in which a substantially continuous array of receivers $R_1, R_2, R_3, \ldots R_n$ may be substituted for receivers 22 and 24. In this system, rather than making a comparison of the signal strength received at two spaced receivers, the array of receivers can give a substantially exact location as to the exit point of the energy flux Qt portion, and therefore substantially the exact deviation of the QT energy component at any time. This deviation, or lack of deviation, will indicate the condition of the fiber/matrix composite structure.

Also illustrated in FIG. 3 is a diagrammatic representation of one form of standard instrumentation which may be utilized to measure the position of QT signals received by any receiver $R_1, R_2, R_3, \ldots R_n$. As shown, each receiver is operatively connected to an amplifier 32 from which amplified signals are fed, for example, to CRT display 34. The CRT display will graphically show the location of the QT component of energy flux along the array, and thus show whether or not there has been any deviation in the QT flux component due to degradation, and if so, how much. For purposes of accuracy, in operation the same energy pulse generator 36 which activates transmitter 14 will also be used to trigger CRT 34 so that the operations will be synchronous.

As already noted, the practice of the present invention does not require the utilization of any information concerning the QL wave, which are not found to deviate as a function of degradation.

In preferred embodiments energy flux transmitter 14 is a source of ultra-sound, such as a piezoelectric transducer. Similarly, in preferred embodiments, receivers 22, 24, or $R_1, R_2, R_3, \ldots R_n$ are also piezoelectric transducers. However, equivalent sources of stress wave transmission and other appropriate suitable receivers may be utilized within the teaching of the practice of the present invention.

While systems showing two receivers and an array of receivers have been shown, any system utilizing a minimum of two receivers can be utilized in the practice of the present invention. The methods and systems of the present invention are suitable for use with any composite structure comprised of any material, so long as the matrix is isotropic and the fibers are arrayed unidirectionally within the matrix.

While the present invention has been described in particular detail with respect to specific systems and structures, it will readily be seen that it can be used to detect deviation in any equivalent composite structure utilizing any equivalent energy wave source, and such uses as will occur to those skilled in the art are intended to be equivalent to the scope and spirit of the present invention as set forth in the appended claims.

What is claimed:

1. A non-destructive, non-invasive method for monitoring, measuring and/or detecting changes in elastic stiffness in a fiber/matrix composite structure composed of an isotropic matrix including fiber material distributed unidirectionally within said matrix, including the steps of:
   locating an energy flux producing transducer to transmit energy flux into said composite structure;
   energizing said transducer so that said composite structure is subjected to traversing energy flux from said transducer; and
   determining the direction which said energy flux takes through said composite structure; and
   wherein the direction of said energy flux through said composite structure is determined by determining the location from which energy flux exits the composite structure.

2. The method of claim 1 wherein said energy flux is acoustic energy.

3. The method of claim 2 wherein said acoustic energy flux is ultra-sonic and upon entering said composite structure is divided into a quasi-longitudinal component and a quasi-transverse component.

4. The method of claim 3 wherein the component of said acoustic energy flux which is measured is the quasi-transverse component.

5. The method of claim 1 wherein the matrix material of said composite structure is selected from binders consisting of thermoset polymers, thermoplastic polymers, and metals.

6. The method of claim 1 wherein the fiber materials of said composite structure are selected from the group consisting of graphite, carbon, glass, polymers, boron and tungsten and mixtures thereof.

7. The method of claim 6 wherein said fibers constitute from about 1% to about 91%, by volume, of said composite structure.

8. The method of claim 6 wherein said fibers constitute from about 50% to about 70%, by volume, of said composite structure.

9. A system for monitoring, measuring and/or detecting changes in elastic stiffness in fiber/matrix composite structures composed of an isotropic matrix including unidirectional fibers including:
   an energy flux producing transducer;
   at least two energy flux receivers located at a position opposed to said transducer with said to-be-tested composite located intermediate said transducer and said receivers, at least one such receiver being positioned to receive substantial energy flux from said energy flux transducer when the elastic stiffness of said composite structure is non-degraded, and at least one such receiver being positioned to receive substantial energy flux from said energy flux transducer when the elastic stiffness of said composite structure is degraded; and
   means to measure the energy flux received by each receiver; whereby energy flux produced by said transducer is transmitted into and through said to-be-tested composite structure, and said receivers indicate the relative strength of the signals received by each receiver, so that changes in the elastic stiffness condition of said structure may be determined by measuring the change in direction of the energy flux.

10. The system of claim 9 wherein said two or more receivers are a substantially continuous array of receivers.

11. The system of claim 9 wherein said flux producing transducer is a source of ultra-sound.

12. The system of claim 11 wherein said source of ultra-sound is a piezoelectric transducer.

13. The system of claim 9 wherein at least one said receiver is a piezoelectric transducer.

* * * * *